US010799660B2

(12) United States Patent
Klurfeld

(10) Patent No.: US 10,799,660 B2
(45) Date of Patent: Oct. 13, 2020

(54) WEARABLE MULTIFUNCTIONAL INHALER, VAPORIZER WATCH

(71) Applicant: Peter Daniel Klurfeld, Encino, CA (US)

(72) Inventor: Peter Daniel Klurfeld, Encino, CA (US)

( * ) Notice: Subject to any disclaimer, the term of this patent is extended or adjusted under 35 U.S.C. 154(b) by 62 days.

(21) Appl. No.: 15/264,508

(22) Filed: Sep. 13, 2016

(65) Prior Publication Data

US 2017/0106152 A1  Apr. 20, 2017

Related U.S. Application Data

(60) Provisional application No. 62/218,582, filed on Sep. 15, 2015.

(51) Int. Cl.
| | |
|---|---|
| A61M 16/00 | (2006.01) |
| A61M 11/04 | (2006.01) |
| A61M 11/00 | (2006.01) |
| A61M 15/00 | (2006.01) |
| A61M 11/06 | (2006.01) |
| A61M 16/04 | (2006.01) |
| A61M 16/06 | (2006.01) |
| A61M 16/08 | (2006.01) |
| A45F 5/00 | (2006.01) |
| A61M 16/16 | (2006.01) |

(52) U.S. Cl.
CPC ........ *A61M 16/0493* (2014.02); *A61M 11/00* (2013.01); *A61M 11/041* (2013.01); *A61M 11/06* (2013.01); *A61M 15/00* (2013.01); *A61M 16/021* (2017.08); *A61M 16/06* (2013.01); *A61M 16/0683* (2013.01); *A61M 16/085* (2014.02); *A61M 16/0875* (2013.01); *A45F 2005/008* (2013.01); *A61M 16/161* (2014.02); *A61M 2202/0275* (2013.01); *A61M 2210/0618* (2013.01); *A61M 2210/0625* (2013.01); *A61M 2230/432* (2013.01); *A61M 2230/50* (2013.01)

(58) Field of Classification Search
CPC ............ A45F 2005/006–008; A61M 2209/088
See application file for complete search history.

(56) References Cited

U.S. PATENT DOCUMENTS

| | | | |
|---|---|---|---|
| 3,178,912 A | 4/1965 | Christenson | |
| 3,379,491 A | 4/1968 | Houle | |
| 3,695,815 A | 10/1972 | Schaefer | |
| 3,816,056 A | 6/1974 | Brown | |
| 4,086,756 A | 5/1978 | Drake | |
| 6,223,744 B1 * | 5/2001 | Garon | A61M 15/00 128/200.14 |
| 9,943,111 B2 * | 4/2018 | Cameron | H05B 3/44 |

(Continued)

*Primary Examiner* — Rachel T Sippel
(74) *Attorney, Agent, or Firm* — William J. Benman; Benman, Brown & Williams

(57) ABSTRACT

A compact wearable inhaler, vaporizer and/or atomizer is addressed by the wearable multifunctional inhaler, vaporizer and smartwatch of the present invention. In the best mode, the invention includes a housing with a chamber having at least port; a lid adapted to engage the housing and open the chamber in a first position and close the chamber in a second position; a source of inhalant mounted within the housing for sourcing inhalant into the chamber via the ports; and an mechanism coupled to the housing for wearing the device. The source of inhalant may be a vaporizer, pipe, inhaler or atomizer.

20 Claims, 2 Drawing Sheets

(56) References Cited

U.S. PATENT DOCUMENTS

| | | | |
|---|---|---|---|
| 2006/0126444 A1* | 6/2006 | Ellner | G04B 37/127 368/246 |
| 2010/0050690 A1 | 3/2010 | Woodward | |
| 2010/0083963 A1* | 4/2010 | Wharton | A45F 5/00 128/203.15 |
| 2010/0163041 A1* | 7/2010 | Hyde | A61D 7/04 128/203.15 |
| 2010/0206307 A1* | 8/2010 | Imai | A61M 11/007 128/203.14 |
| 2011/0089078 A1* | 4/2011 | Ziemba | A45C 1/04 206/570 |
| 2014/0174458 A1* | 6/2014 | Katz | A24F 47/008 131/200 |
| 2014/0261488 A1* | 9/2014 | Tucker | A24F 47/008 131/328 |
| 2014/0334804 A1* | 11/2014 | Choi | A61M 15/06 392/404 |
| 2015/0208729 A1* | 7/2015 | Monsees | A61M 11/042 131/329 |
| 2015/0230521 A1* | 8/2015 | Talon | H05B 1/0244 131/328 |
| 2015/0264978 A1* | 9/2015 | Arnel | A24F 47/002 131/329 |
| 2015/0313275 A1* | 11/2015 | Anderson | A24B 15/10 131/352 |
| 2015/0320116 A1* | 11/2015 | Bleloch | A61M 15/06 219/628 |
| 2016/0089508 A1* | 3/2016 | Smith | A61M 15/06 128/200.16 |
| 2016/0101248 A1* | 4/2016 | Baldwin | A61M 15/0021 128/200.14 |
| 2016/0198767 A1* | 7/2016 | Verleur | H05B 1/0202 392/386 |
| 2017/0095624 A1* | 4/2017 | Davidson | A61K 9/007 |
| 2017/0157341 A1* | 6/2017 | Pandya | A61M 11/042 |

\* cited by examiner

WEARABLE MULTIFUNCTIONAL INHALER, VAPORIZER WATCH

REFERENCE TO RELATED APPLICATION

This application claims priority from a Provisional Application filed Sep. 15, 2015, by P. D Klurfeld et al., entitled WEARABLE VAPORIZER AND/OR ATOMIZER WITH ADDITIONAL CAPABILITIES, application No. 62/218,582.

BACKGROUND OF THE INVENTION

Field of the Invention

The present invention relates to health related devices. More specifically, this invention relates to inhalers and vaporizers.

Description of the Related Art

As is well-known in the art, inhalers use compressed-gas propellant to deliver a metered dose of medicine. When the inhaler is activated, a fixed amount of the medicine is suspended in the propellant and is expelled from the mouthpiece of the inhaler. Vaporizers are devices used to turn active ingredients of plant material and/or other herbs or blends to vapor for the purpose of inhalation. An atomizer is a device for emitting water, perfume, or other liquids as a fine spray.

Currently, there is a need in the art for a compact inhaler, vaporizer or atomizer. A compact implementation of an inhaler, vaporizer or atomizer would allow for the device to be worn on the body thereby making it available to a patient or user for medical emergencies or simple convenience.

SUMMARY OF THE INVENTION

The need in the art for a compact wearable inhaler, vaporizer and/or atomizer is addressed by the wearable multifunctional inhaler, vaporizer and smartwatch of the present invention. In the best mode, the invention includes a housing with a chamber having at least one port; a lid adapted to engage the housing and open the chamber in a first position and close the chamber in a second position; a source of inhalant mounted within the housing for sourcing inhalant into the chamber via the ports; and a mechanism coupled to the housing for wearing the device.

The source of inhalant may be a vaporizer, pipe, inhaler or atomizer. In one embodiment, the source of inhalant includes a fluid reservoir and the device includes a wick having a distal end and a proximal end. The distal end is in fluid communication with the fluid and includes a heating element mounted in thermal proximity to the proximal end of the wick. In this embodiment, the device includes a source of electrical potential disposed in the chamber and electrically coupled to the heating element. A switch is included for activating the heating element. The switch may be mounted on the housing. In the best mode, the smartwatch display is a touch screen display through which the switch is implemented. The smartwatch mounted on or in the lid coupled to electrical contacts in the lid and housing. Either the smartwatch, or an associated smart phone or other computer to which it is coupled via a wireless connection, includes software for a variety of functions including tracking status of the device, level of inhalant remaining, activation of the heating element and/or displaying the status of same.

The device may be coupled to an external inhaler and may be worn via a wristband, armband, anklet, belt or necklace.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

The compact wearable inhaler, vaporizer and/or atomizer of the present invention is shown in FIGS. 1-4.

Figure 1:
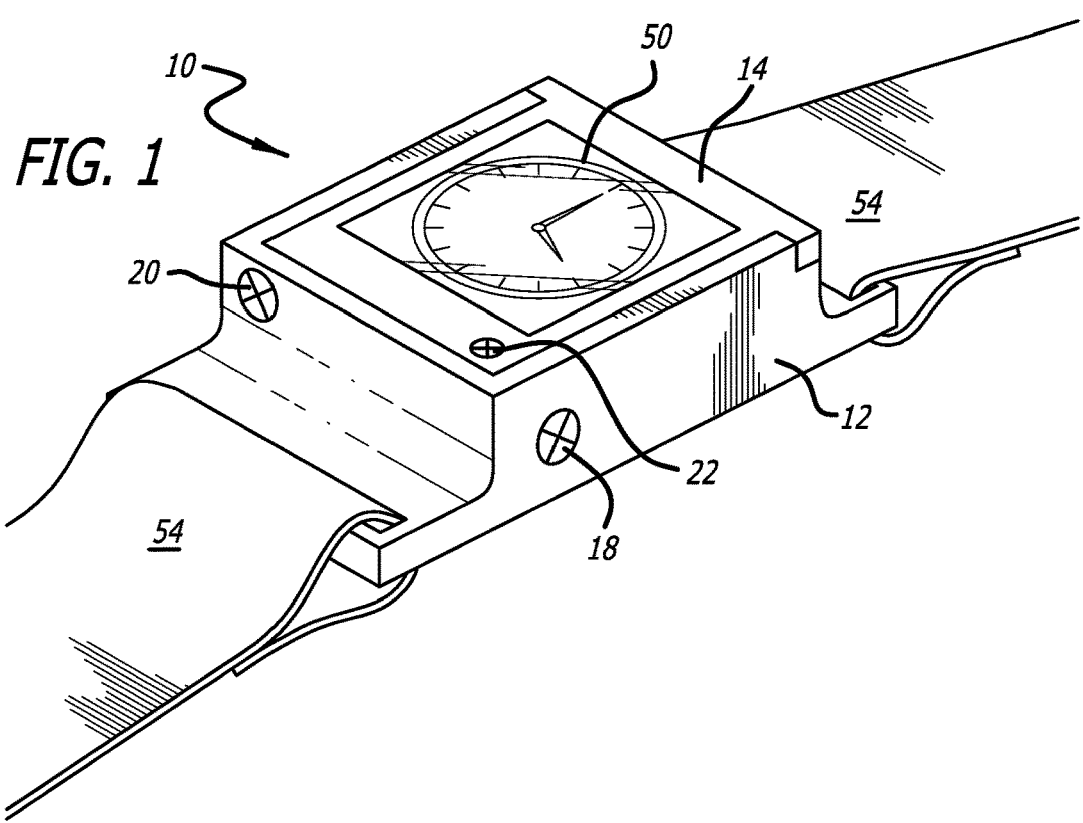
FIG. 1 is a perspective view of an illustrative embodiment of the compact wearable multifunctional inhaler, vaporizer and smartwatch of the present invention with the lid thereof in a closed position.

FIG. 1 is a perspective view of an illustrative embodiment of the compact wearable multifunctional inhaler, vaporizer and smartwatch of the present invention with the lid thereof in a closed position.

Figure 2:
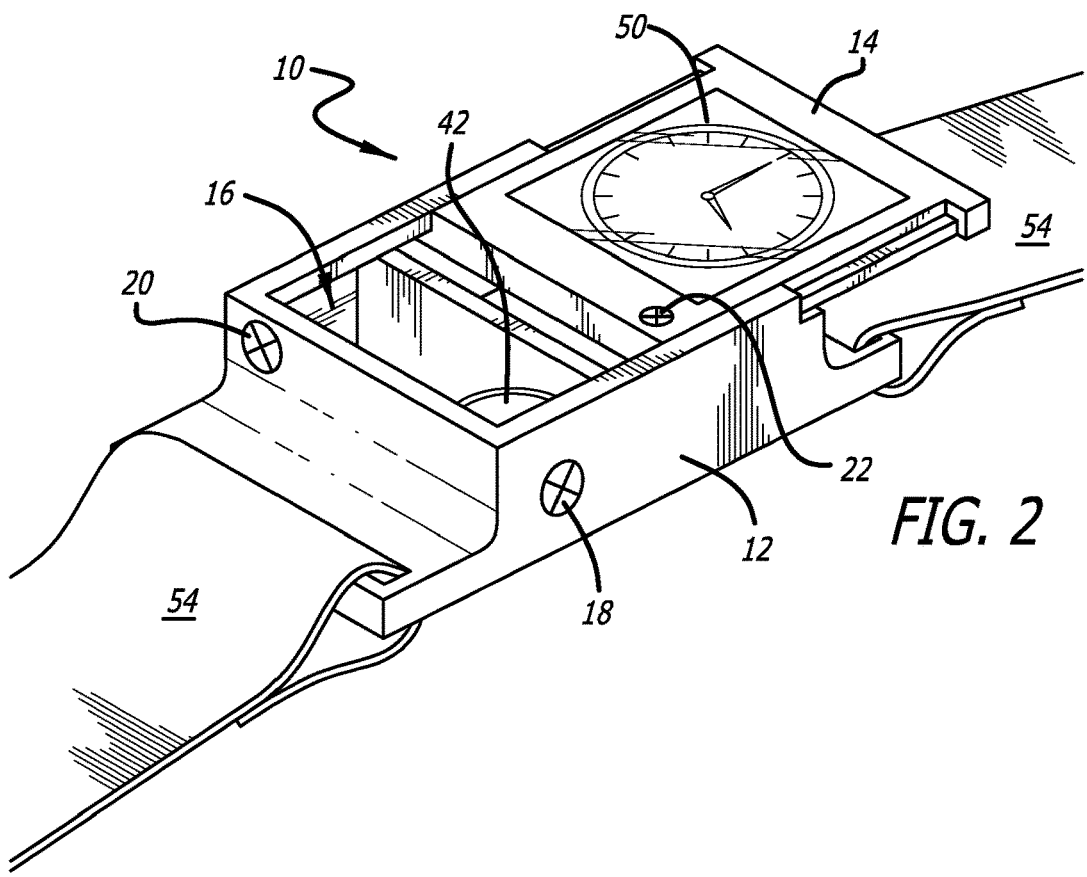
FIG. 2 is a perspective view of an illustrative embodiment of the compact wearable multifunctional inhaler, vaporizer and smartwatch of FIG. 1 with the lid thereof in an open position.

FIG. 2 is a perspective view of an illustrative embodiment of the compact wearable multifunctional inhaler, vaporizer and smartwatch of FIG. 1 with the lid thereof in an open position.

Figure 3:
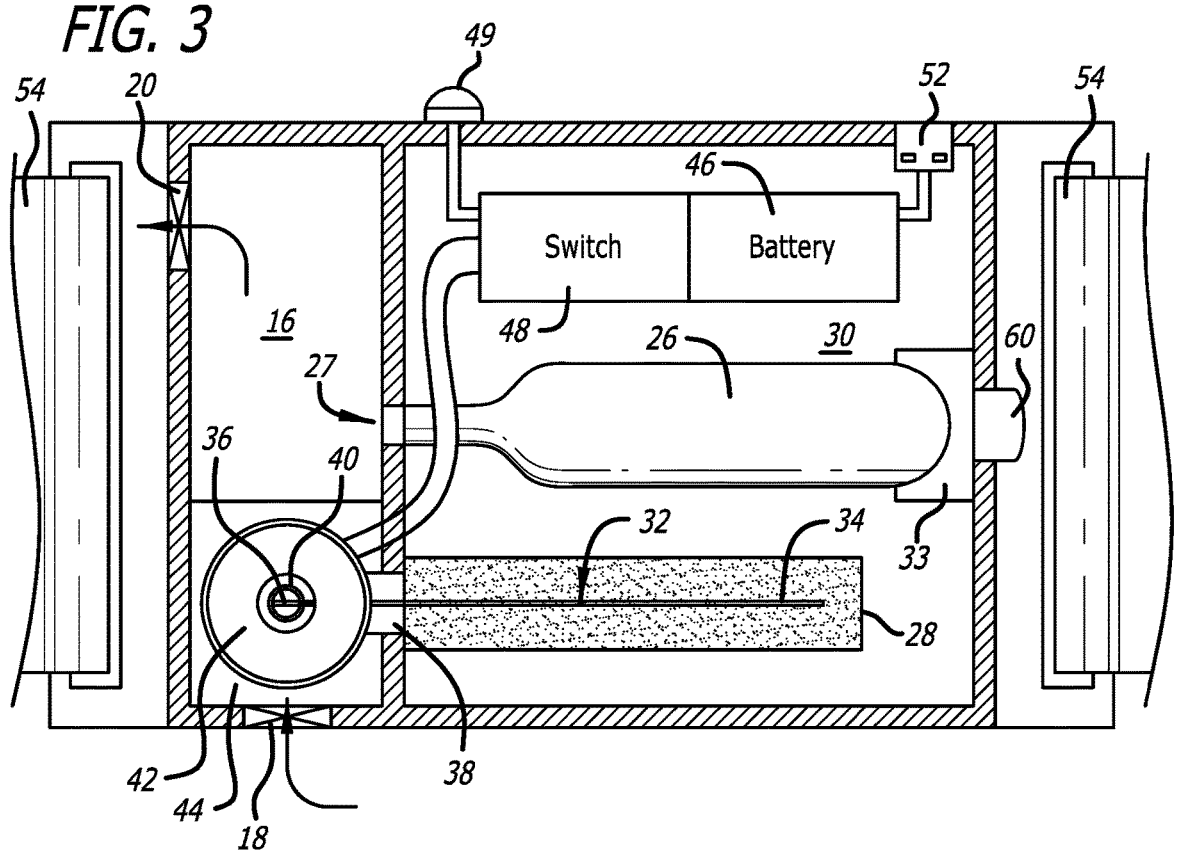
FIG. 3 is a top plan sectional view of the compact wearable multifunctional inhaler, vaporizer and smartwatch of FIG. 1.

FIG. 3 is a top plan sectional view of the compact wearable multifunctional inhaler, vaporizer and smartwatch of FIG. 1.

Figure 4:
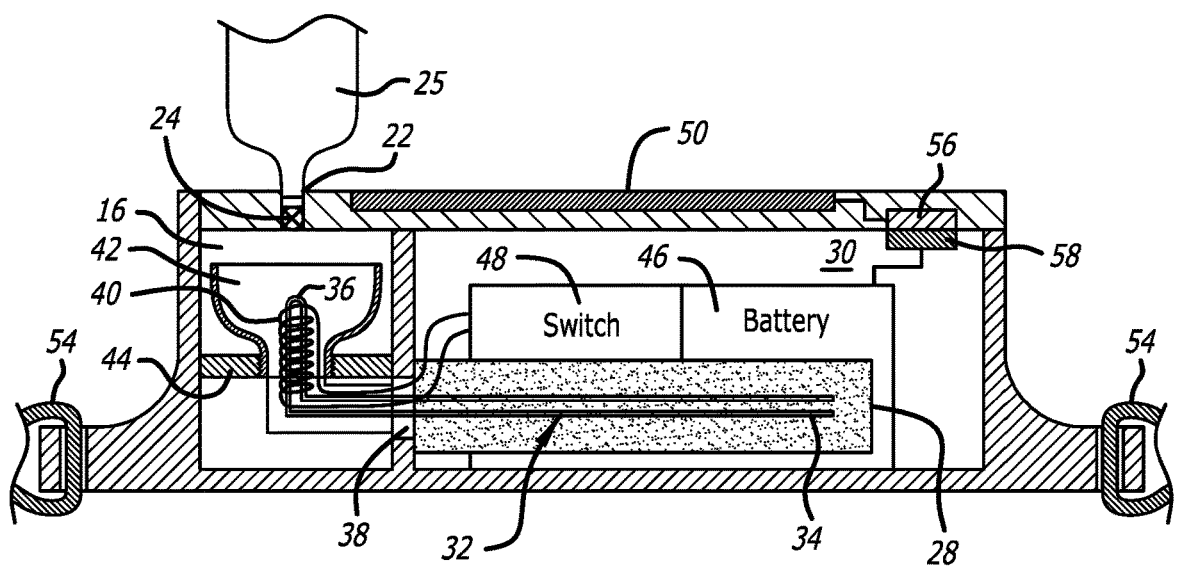
FIG. 4 is a sectional side view of the compact wearable multifunctional inhaler, vaporizer and smartwatch of FIG. 1 with an optional external inhaler capsule.

FIG. 4 is a sectional side view of the compact wearable multifunctional inhaler, vaporizer and smartwatch of FIG. 1 with an optional external inhaler capsule.

As shown in the Figures, the wearable multifunctional inhaler, vaporizer and smartwatch 10 of the present invention includes a housing 12 with a lid 14 and a first chamber 16 therein. As discussed more fully below, the lid 14 is adapted to engage the housing 12 and open the chambers therein in a first position (shown in FIG. 2) and close the chambers and provide a substantially airtight seal in a second position thereof (shown in FIG. 1).

An input port 18 and an output port 20 are provided in the housing 12 to effect fluid communication into and out of the first chamber 16 respectively. In the best mode, each port is fitted with a one way valve such that the input port 18 only allows gas or airflow into the first chamber 16 and the output port 20 only allow gas, inhalant or airflow out of the first chamber 16. A second output port 22 is provided in the lid 14.

As shown in FIGS. 3 and 4, the present invention may be implemented as an inhaler with an external canister or an internal canister. In an internal inhaler canister implementation, a removable pressurized canister 26 of inhaler medicine is mounted in the second chamber 30, in lieu of the vaporizer discussed below, in alignment with a port 27 (and optional valve (not shown)). The canister is held in place by a flexible or rigid retainer 33. The inhaler canister 26 is activated by pressing a button 60 mounted at a rear thereof that extends through the housing 12 of the device 10 for external activation. Inhaler is then sprayed into the chamber 16 and subsequently evacuated by an inhale by the user via the output port 20.

The second output port 22 is included along with a fixture 24 to enable coupling of an optional vaporizing tube or external inhalant canister 25. (See FIG. 4.) If an external canister 25 is used, the fixture 24 allows for inflow of inhalant into the chamber 16. The medicinal gas is then evacuated from the chamber 16 via the output port 20.

In a vaporizer implementation, a removable fluid reservoir 28, filled with vaporizer liquid, is mounted in a second chamber 30 along with or in lieu of the inhaler canister 26. The distal end 34 of a wick 32 extends into the fluid reservoir 28 and draws fluid therefrom via a wicking action to the proximal end 36 of the wick 32. The wick 32 extends from the second chamber 30 into the first chamber 16 via an inter-chamber port 38 there between. The proximal end 36 of the wick 32 is orthogonal to the longitudinal axis of the wick to yield an L-shaped dog leg segment that extends into a bowl 42 supported on a platform 44 in the first chamber 16. The proximal end 36 of the wick 32 is suspended at the base of the bowl in an upright orientation and surrounded by a heating element 40. In the illustrative embodiment, the heating element is a coil. However, those of ordinary skill in the art will appreciate that other safe and effective heating elements could be used such as spark ignition devices, diode lasers, etc., without departing from the scope of the present teachings.

The heating coil 40 is powered by a rechargeable battery 46 though a switch 48. The switch 48 may be activated by a button 49 mounted on the housing or a touch screen provided by a smartwatch 50 mounted on or in the lid 14.

If a vaporizing tube (not shown) is inserted, the fixture 24 allows for outflow of vapor from the chamber 16.

As is well known in the art, a smartwatch is an electronic circuit with a processor, a memory fixed in a tangible medium, a wireless transceiver and a touchscreen display. Software for implementing a variety of functions is provided in either the smartwatch, or an associated smart phone or other computer to which it is coupled via a wireless connection. Those functions include by way of example tracking and displaying the status of the device, scheduling medication use, monitoring and displaying the level of inhalant remaining via a sensor and LED (not shown) mounted in the housing and electrically coupled to the smartwatch or an integrated rear camera, activation of the heating element and/or displaying the status of same, sending a notification to a friend or family member that the emergency dose of inhalant has been used, etc. The software provides data to an associated health application on a user's smart phone. When the heating element is activated, the display on the device is programmed to change to show a flame or other symbol or image to indicate that the heating element is activated.

Battery power to the coil 40 may also be provided by the smartwatch 50 as well. The battery 46 and the smartwatch 50 are coupled via contacts 56 and 58. The battery 46 may be recharged through a USB connection 52.

In the illustrative embodiment, the device 10 is coupled to a wristband 54 enabling it to be worn as a watch. However, the device 10 may also be removed and worn as armband, anklet, bracelet, belt or necklace or carried in a pocket, purse or pouch. The mounting arrangement(s), e.g. wristband, bracelet, belts, etc., can provide additional battery and inhalant storage compartments.

In other embodiments, the device may be used to vaporize solid as well as liquid organic and inorganic herbs, chemicals, compounds and medicines. A breath freshener may be used in place of the inhalant. The device may be used as a pipe to burn tobacco and/or other plants. The smartwatch may be replace with a simple plastic or glass lid and it may be tinted or transparent. The device may be worn upside down and used to read a user's pulse. With the smartwatch, the device could be used as a thermometer and could be solar powered via a solar cell mounted on the lid 14 or on the wristband 54.

The housing and lid may be constructed of stainless steel, aluminum, plastic, ceramic, wood or other suitable material.

Those having ordinary skill in the art and access to the present teachings will recognize additional modifications, applications and embodiments within the scope thereof. For example, the invention is not limited to the size, shape, number or location of the input or output ports used in connection with the device.

It is therefore intended by the appended claims to cover any and all such applications, modifications and embodiments within the scope of the present invention.

What is claimed is:

1. A wearable multifunctional inhalation device comprising:
   a device for displaying the current time of day having a housing with a chamber and at least two ports, the at least two ports comprising an inlet port and an outlet port, in fluid communication with the chamber, said housing further including first and second apertures extending through the housing on opposing ends of the housing for receiving and retaining a wrist band and a third aperture operationally coupled to the chamber through a second outlet port and adapted to be accessible externally when the inhalation device is fully assembled;
   a first source of inhalant including a fluid reservoir in communication with a wick, both of which are mounted within said housing for sourcing inhalant into said chamber, said wick having a distal end and a proximal end, said distal end being in fluid communication with said fluid reservoir and said proximal end being in operational proximity to said heating element;
   a second source of inhalant mounted within said housing in fluid communication with said chamber, said second source of inhalant including a pressurized canister without a wick positioned entirely within the housing activated by a button on a wall of the housing;
   a heating element disposed within said housing for heating said wick;
   a source of electrical potential disposed in said housing and electrically coupled to said heating element;
   a sensor mounted in said housing;
   a switch including an electronic circuit mounted in said housing for activating said heating element, said electronic circuit including a wireless transceiver, a processor in communication therewith, and a memory fixed in a tangible medium, said processor further including software stored in said memory for execution by said processor, said software including:
      a code for activating said heating element and displaying a status of said heating element on a touch screen display mounted within said housing and a code for monitoring the status of the inhalant and/or said source of electrical potential;

a transparent timepiece lid adapted to engage said housing via a sliding linear translation movement along a longitudinal axis of the device; and a fitting for coupling said device to an external inhaler.

2. A wearable multifunctional inhalation device comprising:

a compact housing with a first chamber, a second chamber, and a wall between the first and second chambers with first and second inter-chamber ports in the wall to fluidly connect the first and second chambers;

a fluid inhalant reservoir mounted within the second chamber;

a wick operationally coupled to the fluid reservoir that extends from the second chamber to the first chamber via the first inter-chamber port;

a heating element mounted in the first chamber for heating the wick;

an inlet port operationally coupled to the first chamber;

an outlet port coupled to the first chamber and adapted to be accessible externally when the inhalation device is fully assembled; and a pressurized canister without a wick positioned entirely within the housing activated by a button on a wall of the housing.

3. The invention of claim 2 wherein the fluid reservoir is removable.

4. The invention of claim 2 wherein said pressurized canister is removably mounted within the second chamber to source inhalant into the first chamber via the second inter-chamber port.

5. The invention of claim 2 further including a battery mounted within the second chamber and coupled to said heating element and a switch operationally coupled between the battery and the heating element and mounted within the second chamber.

6. The invention of claim 2 further including a bowl within which the heating element is mounted in the first chamber and a platform for supporting the bowl and heating element in the first chamber.

7. The invention of claim 2 wherein the housing is rectangular.

8. The invention of claim 2 further including a lid for closing the first and second chambers.

9. The invention of claim 8 wherein the lid closes the first and second chambers via a sliding movement.

10. The invention of claim 9 wherein the lid includes a second outlet port that communicates with the first chamber.

11. The invention of claim 9 further including a timepiece mounted on the lid for displaying the current time of day.

12. The invention of claim 11 further including means for enabling the timepiece to display a status of the device.

13. The invention of claim 11 further including means for enabling the timepiece to display a schedule for medication use.

14. The invention of claim 11 further including means for enabling the timepiece to display a level of inhalant.

15. The invention of claim 11 further including means for enabling the timepiece to display activation of the heating element.

16. The invention of claim 11 further including means for enabling the device to send a notification in case of emergency.

17. The invention of claim 11 further including means for enabling the device to send data to a health app.

18. The invention of claim 11 further including means for enabling the timepiece to display a flame or other symbol to indicate that the heating element is activated.

19. A wearable multifunctional inhalation device comprising:

a compact rectangular housing with a first chamber, a second chamber, a wall between the first and second chambers with first and second inter-chamber ports in the wall to fluidly connect the first and second chambers;

a removable fluid inhalant reservoir mounted within the second chamber;

a removable pressurized inhalation canister without a wick mounted entirely within the second chamber to source inhalant into the first chamber via the second inter-chamber port;

a wick operationally coupled to the fluid reservoir that extends from the first chamber to the second chamber via the first inter-chamber port;

a heating element disposed within the first chamber for heating the wick;

at least one inlet port and at least one outlet port operationally coupled to the first chamber;

a lid for closing the first and second chambers via a sliding movement and an externally accessible button mounted from the canister through a wall of the housing for activation of the canister.

20. A wearable multifunctional inhalation device comprising:

a compact housing with a first chamber, a second chamber, and a wall between the first and second chambers with first and second inter-chamber ports in the wall to fluidly connect the first and second chambers;

a fluid inhalant reservoir mounted within the second chamber;

a wick operationally coupled to the fluid reservoir that extends from the second chamber to the first chamber via the first inter-chamber port;

a heating element mounted in the first chamber for heating the wick;

an inlet port operationally coupled to the first chamber;

an outlet port coupled to the first chamber;

a lid adapted to open and close said housing via a sliding linear translation movement along a longitudinal axis of the housing; and a pressurized canister without a wick positioned entirely within the housing activated by a button on a wall of the housing.

* * * * *